United States Patent [19]
Hemmings et al.

[11] Patent Number: 6,040,164
[45] Date of Patent: Mar. 21, 2000

[54] NUCLEIC ACIDS ENCODING NUCLEAR DBF2-RELATED (NDR) KINASES

[75] Inventors: Brian Arthur Hemmings, Bettingen; Thomas Anders Millward, Basel, both of Switzerland

[73] Assignee: Novartis AG, Basel, Switzerland

[21] Appl. No.: 09/338,132

[22] Filed: Jun. 22, 1999

Related U.S. Application Data

[62] Division of application No. 08/860,150, filed as application No. PCT/EP95/05052, Dec. 20, 1995, Pat. No. 5,981,205.

[30] Foreign Application Priority Data

Dec. 22, 1994 [DE] Germany .............................. 94810746

[51] Int. Cl.$^7$ .............................. C12N 9/02; C12N 15/00; C12P 21/06
[52] U.S. Cl. ........................ 435/189; 435/183; 435/69.1; 435/320.1; 435/252.3; 435/325
[58] Field of Search .................................... 435/189, 183, 435/69.1, 325, 252.3, 320.1

[56] References Cited

FOREIGN PATENT DOCUMENTS

WO 9417180   8/1994   WIPO .

OTHER PUBLICATIONS

Cooper et al., Meth. in Enzymol., vol. 99, pp. 387–402 (1983).

Dang et al., Mol. Cell Biol., vol. 8, (10) pp. 4048–4054 (1988).

Dowell et al., Science, vol. 265, pp 1243–1246 (1994).

Ellis et al., Cell vol. 45, pp. 721–732 (1986).

Hanks et al., Meth. Enzymol, vol. 200, pp. 38–62 (1991).

Hendrix et al., The Journal of Biological Chemistry, vol. 268, No. 10, pp. 7330–7337 (1993).

Millward et al., Annual Report FMI, vol. 1993, P. 44 (1995).

Millward et al., Experientia, vol. 50: A17 S05–24 (1994).

Millward et al., PNAS USA, vol. 92, pp. 5022–5026 (1995).

Millward et al., Poster presented at the USGEB meeting of Mar. $17^{th}/18^{th}$ 1994.

Smith et al., Gene, vol. 67, pp. 31–40 (1988).

Waterston et al., Nat. Genet., vol. 1, pp. 114–123 (1992).

*Primary Examiner*—Karen Cochrane Carlson
*Attorney, Agent, or Firm*—Gregory D. Ferraro

[57] ABSTRACT

The current invention describes the identification of a novel widely-expressed human and *D. melanogaster* serine/threonine protein kinase (designated nuclear, Dbf2-related kinase, or Ndr; previously referred to as Ndr) and the use of this kinase for the identification of agonists and antagonists. The kinase is a nuclear protein and contains a short basic peptide, KRKAETWKRNRR, responsible for the nuclear accumulation.

5 Claims, No Drawings

SEQUENCE LISTING

<160> NUMBER OF SEQ ID NOS: 18

<210> SEQ ID NO 1
<211> LENGTH: 2101
<212> TYPE: DNA
<213> ORGANISM: Drosophila melanogaster
<220> FEATURE:
<221> NAME/KEY: CDS
<222> LOCATION: (132)..(1499)

<400> SEQUENCE: 1

```
gaattcggca cgagtgcatt ggcaagtgca taactcctca ccacacacac gcacacgcac      60
cgacatcgca gggagcacac acacaagccc caaataggac cgaggtgacc aggacaaaaa     120
ccccagctta g atg atg agc agc aga acg cag gac gcg gac ggt gcc tcg     170
```

```
            Met Met Ser Ser Arg Thr Gln Asp Ala Asp Gly Ala Ser
             1               5                  10 atc aga ttc agc gac cac aca ctg gac aag gcc acc aag gcc aag gtg         218
Ile Arg Phe Ser Asp His Thr Leu Asp Lys Ala Thr Lys Ala Lys Val
 15                  20                  25 acg ttg gag aac tac tac agc aac ctg gtg acg cag tat ggc gag cga         266
Thr Leu Glu Asn Tyr Tyr Ser Asn Leu Val Thr Gln Tyr Gly Glu Arg
 30                  35                  40                  45 aag cag cgc ctc gca aag ctg gag gct cag ctg aag gac gag agc ttg         314
Lys Gln Arg Leu Ala Lys Leu Glu Ala Gln Leu Lys Asp Glu Ser Leu
                 50                  55                  60 tcg gag gcg cag cgc cag gag aag cgt ctg cag cat gcc cag aag gag         362
Ser Glu Ala Gln Arg Gln Glu Lys Arg Leu Gln His Ala Gln Lys Glu
             65                  70                  75 acg gag tat ctc cgg ctg aag cga ttg cgc ctc ggt gtg gag gac ttt         410
Thr Glu Tyr Leu Arg Leu Lys Arg Leu Arg Leu Gly Val Glu Asp Phe
         80                  85                  90 gag gcc ctc aaa gtc atc gga cgc ggc gcg ttc ggt gaa gtg cgt ttg         458
Glu Ala Leu Lys Val Ile Gly Arg Gly Ala Phe Gly Glu Val Arg Leu
         95                 100                 105 gtg cag aaa aag gac act gga cat gtg tgc gcc atg aag gtg ctg cgc         506
Val Gln Lys Lys Asp Thr Gly His Val Cys Ala Met Lys Val Leu Arg
110                 115                 120                 125 aaa gcg gac atg ctg gaa aag gag cag gtg gca cac gta cgc gcc gag         554
Lys Ala Asp Met Leu Glu Lys Glu Gln Val Ala His Val Arg Ala Glu
                130                 135                 140 ggt ctg cat gtc ctg gtc gag gcc gat cat cag tgg gtg gtg aag atg         602
Gly Leu His Val Leu Val Glu Ala Asp His Gln Trp Val Val Lys Met
            145                 150                 155 tac tac agt ttc cag gat ccc gtc aat tta tat ttg ata atg gag ttc         650
Tyr Tyr Ser Phe Gln Asp Pro Val Asn Leu Tyr Leu Ile Met Glu Phe
        160                 165                 170 ttg cct ggt ggt gat atg atg acg ctt tta atg aag aag gac acg cta         698
Leu Pro Gly Gly Asp Met Met Thr Leu Leu Met Lys Lys Asp Thr Leu
        175                 180                 185 tcc gag gag ggc aca cag ttc tat atc agt gag acg gca ttg gcg atc         746
Ser Glu Glu Gly Thr Gln Phe Tyr Ile Ser Glu Thr Ala Leu Ala Ile
190                 195                 200                 205 gat tct att cac aaa ctc ggt ttc ata cac agg gat atc aag ccc gat         794
Asp Ser Ile His Lys Leu Gly Phe Ile His Arg Asp Ile Lys Pro Asp
                210                 215                 220 aac ttg ctg ctg gac gcg cga ggg cat ctg aag ctc tcc gac ttc gga         842
Asn Leu Leu Leu Asp Ala Arg Gly His Leu Lys Leu Ser Asp Phe Gly
            225                 230                 235 ctg tgc act ggc tta aag aag tcg cat cga aca gac ttt tat cgg gac         890
Leu Cys Thr Gly Leu Lys Lys Ser His Arg Thr Asp Phe Tyr Arg Asp
        240                 245                 250 ttg tcg cag gcg aaa cca tcc gat ttt ata ggc acg tgc gcc agt ccg         938
Leu Ser Gln Ala Lys Pro Ser Asp Phe Ile Gly Thr Cys Ala Ser Pro
    255                 260                 265 atg gac tcc aag cga cgt gcc gag tcg tgg aag cga aat cga cgc gcc         986
Met Asp Ser Lys Arg Arg Ala Glu Ser Trp Lys Arg Asn Arg Arg Ala
270                 275                 280                 285 ctc gcc tac agc acc gtg gga acg ccg gac tat att gca ccc gaa gta        1034
Leu Ala Tyr Ser Thr Val Gly Thr Pro Asp Tyr Ile Ala Pro Glu Val
                290                 295                 300 ttt ctg cag act ggc tac gga ccc gcc tgc gac tgg tgg tcc ctg gga        1082
Phe Leu Gln Thr Gly Tyr Gly Pro Ala Cys Asp Trp Trp Ser Leu Gly
            305                 310                 315
```

-continued

```
gtc atc atg tac gaa atg ctg atg ggc tat cct cca ttc tgc tcg gac      1130
Val Ile Met Tyr Glu Met Leu Met Gly Tyr Pro Pro Phe Cys Ser Asp
        320                 325                 330 aat ccc cag gac acc tac cgc aag gtg atg aac tgg cgc gag acg ctg      1178
Asn Pro Gln Asp Thr Tyr Arg Lys Val Met Asn Trp Arg Glu Thr Leu
335                 340                 345 ata ttt ccc cca aga gat ccc ata tcg gag gag gcc aag gag acg atc      1226
Ile Phe Pro Pro Arg Asp Pro Ile Ser Glu Glu Ala Lys Glu Thr Ile
350                 355                 360                 365 atc aac ttc tgc tgc gag gcc gat cgc cgc tgg gtt cca gcg tcg tct      1274
Ile Asn Phe Cys Cys Glu Ala Asp Arg Arg Trp Val Pro Ala Ser Ser
            370                 375                 380 gga gga tct gaa gtc gtg ccg ttc ttc cgg gga gtt gac tgg gag cac      1322
Gly Gly Ser Glu Val Val Pro Phe Phe Arg Gly Val Asp Trp Glu His
                385                 390                 395 ata cta gcc gcg cca tac ctt gag gtg cgc tca atc gac gat acg tcc      1370
Ile Leu Ala Ala Pro Tyr Leu Glu Val Arg Ser Ile Asp Asp Thr Ser
            400                 405                 410 aac ttc gac gag ttt ccc gat gtg tcg ctg gag ata cca tcg gcg ccc      1418
Asn Phe Asp Glu Phe Pro Asp Val Ser Leu Glu Ile Pro Ser Ala Pro
        415                 420                 425 ata ccg cag ggc ggt gag att gcg aag gac tgg gtc ttt atc aac tac      1466
Ile Pro Gln Gly Gly Glu Ile Ala Lys Asp Trp Val Phe Ile Asn Tyr
430                 435                 440                 445 acg tac aaa cga ttc gag gtg cga aat ttg gag tgaatccacc agagcaggaa   1519
Thr Tyr Lys Arg Phe Glu Val Arg Asn Leu Glu
                450                 455 ctggagcagg agcagtagca gtagcagctt gaaggttgcc gcactttgcc acccatttta   1579
tcaccaccac agccgtcgtc tctctaacac catcaccacc aagagcattc tcacgctaaa   1639
ctgaaatccc cgattttcct ttttgaatgt cttacctaca tgtgtattta aatactagct   1699
aacatttgtg attccaaaca agagaagaat atgataacgc gaacaaacga tgtattgtat   1759
gtaaaaagt cttcttagag cgtcgcccgc gcctcgcggt aggttaaacg ctatactaat    1819
cctcaaatgt tcttccatgg ctttgttcaa tccctaatcc cgatcttacg cttaacgttg   1879
tgtttgtaaa ccagttcccc atattaggga cccgttcggc aattctttat atatatatat   1939
attgtttact tattgggcag cagcgaaata cccataaatt tattatttag caaattaaaa   1999
atgttataac ttttaggcca cgttaattgt acgtatatgt tttgtatcaa cttgtaatga   2059
aacaaagtct taatacatag cgaaccccac acacaaaacc ga                      2101
```

<210> SEQ ID NO 2
<211> LENGTH: 456
<212> TYPE: PRT
<213> ORGANISM: Drosophila melanogaster

<400> SEQUENCE: 2

```
Met Met Ser Ser Arg Thr Gln Asp Ala Asp Gly Ala Ser Ile Arg Phe
1               5                   10                  15

Ser Asp His Thr Leu Asp Lys Ala Thr Lys Ala Lys Val Thr Leu Glu
            20                  25                  30

Asn Tyr Tyr Ser Asn Leu Val Thr Gln Tyr Gly Glu Arg Lys Gln Arg
        35                  40                  45

Leu Ala Lys Leu Glu Ala Gln Leu Lys Asp Glu Ser Leu Ser Glu Ala
    50                  55                  60

Gln Arg Gln Glu Lys Arg Leu Gln His Ala Gln Lys Glu Thr Glu Tyr
65                  70                  75                  80
```

```
Leu Arg Leu Lys Arg Leu Arg Leu Gly Val Glu Asp Phe Glu Ala Leu
                 85                  90                  95

Lys Val Ile Gly Arg Gly Ala Phe Gly Glu Val Arg Leu Val Gln Lys
            100                 105                 110

Lys Asp Thr Gly His Val Cys Ala Met Lys Val Leu Arg Lys Ala Asp
        115                 120                 125

Met Leu Glu Lys Glu Gln Val Ala His Val Arg Ala Glu Gly Leu His
    130                 135                 140

Val Leu Glu Ala Asp His Gln Trp Val Val Lys Met Tyr Tyr Ser
145                 150                 155                 160

Phe Gln Asp Pro Val Asn Leu Tyr Leu Ile Met Glu Phe Leu Pro Gly
                165                 170                 175

Gly Asp Met Met Thr Leu Leu Met Lys Lys Asp Thr Leu Ser Glu Glu
            180                 185                 190

Gly Thr Gln Phe Tyr Ile Ser Glu Thr Ala Leu Ala Ile Asp Ser Ile
        195                 200                 205

His Lys Leu Gly Phe Ile His Arg Asp Ile Lys Pro Asp Asn Leu Leu
    210                 215                 220

Leu Asp Ala Arg Gly His Leu Lys Leu Ser Asp Phe Gly Leu Cys Thr
225                 230                 235                 240

Gly Leu Lys Lys Ser His Arg Thr Asp Phe Tyr Arg Asp Leu Ser Gln
                245                 250                 255

Ala Lys Pro Ser Asp Phe Ile Gly Thr Cys Ala Ser Pro Met Asp Ser
            260                 265                 270

Lys Arg Arg Ala Glu Ser Trp Lys Arg Asn Arg Arg Ala Leu Ala Tyr
        275                 280                 285

Ser Thr Val Gly Thr Pro Asp Tyr Ile Ala Pro Glu Val Phe Leu Gln
    290                 295                 300

Thr Gly Tyr Gly Pro Ala Cys Asp Trp Trp Ser Leu Gly Val Ile Met
305                 310                 315                 320

Tyr Glu Met Leu Met Gly Tyr Pro Pro Phe Cys Ser Asp Asn Pro Gln
                325                 330                 335

Asp Thr Tyr Arg Lys Val Met Asn Trp Arg Glu Thr Leu Ile Phe Pro
            340                 345                 350

Pro Arg Asp Pro Ile Ser Glu Glu Ala Lys Glu Thr Ile Ile Asn Phe
        355                 360                 365

Cys Cys Glu Ala Asp Arg Arg Trp Val Pro Ala Ser Ser Gly Gly Ser
370                 375                 380

Glu Val Val Pro Phe Phe Arg Gly Val Asp Trp Glu His Ile Leu Ala
385                 390                 395                 400

Ala Pro Tyr Leu Glu Val Arg Ser Ile Asp Asp Thr Ser Asn Phe Asp
                405                 410                 415

Glu Phe Pro Asp Val Ser Leu Glu Ile Pro Ser Ala Pro Ile Pro Gln
            420                 425                 430

Gly Gly Glu Ile Ala Lys Asp Trp Val Phe Ile Asn Tyr Thr Tyr Lys
        435                 440                 445

Arg Phe Glu Val Arg Asn Leu Glu
    450                 455

<210> SEQ ID NO 3
<211> LENGTH: 404
<212> TYPE: PRT
<213> ORGANISM: Caenorhabditis elegans

<400> SEQUENCE: 3
```

```
Arg Lys Glu Glu Lys Arg Lys Ile His His Ser Lys Glu Thr Asp Tyr
 1               5                  10                  15

Leu Arg Leu Lys Arg Thr Arg Leu Thr Val Asn Asp Phe Glu Ser Leu
            20                  25                  30

Lys Val Ile Gly Arg Gly Ala Phe Gly Glu Val Arg Leu Val Gln Lys
            35                  40                  45

His Asp Thr Gly His Ile Tyr Ala Met Lys Ile Leu Arg Lys Ser Glu
       50                  55                  60

Met Val Glu Lys Glu Gln Thr Ala His Val Arg Ala Glu Arg Asp Ile
 65                 70                  75                  80

Leu Ser Glu Ala Asp Cys Asp Trp Val Val Lys Met Tyr Tyr Ser Phe
                85                  90                  95

Gln Asp Tyr Ser Asn Leu Tyr Leu Val Met Glu Phe Leu Pro Gly Gly
               100                 105                 110

Asp Met Met Thr Leu Leu Ile Lys Lys Asp Thr Leu Thr Glu Glu Ala
           115                 120                 125

Thr Gln Phe Tyr Ile Ala Glu Ala Leu Ala Ile Gln Phe Ile His
       130                 135                 140

Ser Leu Gly Phe Ile His Arg Asp Ile Lys Pro Asp Asn Leu Leu Leu
145                 150                 155                 160

Asp Ala Arg Gly His Val Lys Leu Ser Asp Phe Gly Leu Cys Thr Gly
               165                 170                 175

Leu Lys Lys Phe His Arg Thr Asp His Tyr Arg Asn Trp Pro Ser Thr
           180                 185                 190

Leu Pro Pro Asp Phe Ile Ser Lys Pro Phe Glu Ser Lys Arg Lys Ala
           195                 200                 205

Glu Thr Trp Lys Arg Asn Arg Arg Ala Tyr Ala Tyr Ser Met Val Gly
           210                 215                 220

Thr Pro Asp Tyr Ile Ala Pro Glu Val Phe Gln Pro Asn Gly Tyr Thr
225                 230                 235                 240

Lys Ser Cys Asp Trp Trp Ser Leu Gly Val Ile Met Tyr Glu Met Leu
               245                 250                 255

Ile Gly Tyr Pro Pro Phe Cys Ser Glu Leu Pro Gln Glu Thr Tyr Arg
               260                 265                 270

Lys Val Ile Asn Trp Gln Gln Thr Leu Val Phe Pro Ser Asp Val Pro
           275                 280                 285

Ile Ser Ile Glu Ala Lys Ala Thr Ile Lys Arg Phe Cys Cys Glu Arg
           290                 295                 300

Glu Arg Arg Leu Gly Asn His Gly Gly Leu Asp Glu Ile Lys Gln Cys
305                 310                 315                 320

Pro Phe Val Lys Arg Ile Asp Trp Asn His Ile Arg Glu Arg Pro Pro
               325                 330                 335

Pro Ile Arg Val Thr Val Lys Ser Ile Asp Asp Thr Ser Asn Phe Asp
               340                 345                 350

Asp Phe Pro Asp Glu Asp Leu Thr Trp Pro Thr Ser Thr Leu Ile Arg
               355                 360                 365

Pro Glu Glu Gln Pro Gly Arg Arg Gly Glu Phe Val Asp Phe Thr Tyr
           370                 375                 380

Lys Arg Phe Asp Gly Leu Thr Gln Lys Met Arg Tyr Ser Asp Leu Lys
385                 390                 395                 400

Lys Gln Ala Lys
```

```
<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: modified_base
<222> LOCATION: (14)..(32)
<223> OTHER INFORMATION: bases 14, 17, 26, 29 and 32 are the modified
      base i

<400> SEQUENCE: 4
aatctagaaa rgadacdgar tayytdmgdy tdaa                                 34

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence: PCR primer
<220> FEATURE:
<221> NAME/KEY: modified_base
<222> LOCATION: (11)..(32)
<223> OTHER INFORMATION: bases 11, 23, 26, 29 and 32 are the modified
      base i

<400> SEQUENCE: 5
aaaagcttgg dgcdatrtar tcdggdgtdc cdac                                 34

<210> SEQ ID NO 6
<211> LENGTH: 3018
<212> TYPE: DNA
<213> ORGANISM: Homo sapiens
<220> FEATURE:
<221> NAME/KEY: CDS
<222> LOCATION: (596)..(1990)

<400> SEQUENCE: 6
gaattccggg ccaggcatgg tagcgcatcg ctgtaatccc agctactcgg gaaactgagg       60
tgggagaatc gattgaacct ggaagtggag gttgcggtga gccaagatca tcctgtcgca      120
ctccagcctg ggcaacaaga gcgaaactcc atctcaaaaa gaaaaaaaaa gatatatatg      180
tgtgacttac aggtacaggt aaagttgctt ctggttttct ggttgttgca tggtatttcc      240
tatgcagcca caggtctttta ttttcttact taagtgcctc caacttccca taacacaaat     300
taaggcatga tgaacatcct ctctgtgctg aacatcctgt gtatgtcact tcagaagcct      360
gtgtgacggt ttctttagtc tttataccta ggggtgggat ttctgggtca taggacagta      420
atttatattt atttcactaa gtattctctt tctctggctt ttgttacata ttacctgttt      480
gtcctccaga aaacttgcac caatttacat tcctaccaat agggtaggag agtgcacaat      540
gggtggattc taactccaaa tctaacacct cttcttttct ttgtttctag cagcc atg       598
                                                             Met
                                                               1 gca atg aca ggc tca aca cct tgc tca tcc atg agt aac cac aca aag        646
Ala Met Thr Gly Ser Thr Pro Cys Ser Ser Met Ser Asn His Thr Lys
           5                  10                  15 gaa agg gtg aca atg acc aaa gtg aca ctg gag aat ttt tat agc aac        694
Glu Arg Val Thr Met Thr Lys Val Thr Leu Glu Asn Phe Tyr Ser Asn
     20                  25                  30 ctt atc gct caa cat gaa gaa cga gaa atg aga caa aag aag tta gaa        742
Leu Ile Ala Gln His Glu Glu Arg Glu Met Arg Gln Lys Lys Leu Glu
 35                  40                  45 aag gtg atg gaa gaa gaa ggc cta aaa gat gag gag aaa cga ctc cgg        790
```

```
Lys Val Met Glu Glu Glu Gly Leu Lys Asp Glu Lys Arg Leu Arg
 50                  55                  60                  65 aga tca gca cat gct cgg aag gaa aca gag ttt ctt cgt ttg aag aga        838
Arg Ser Ala His Ala Arg Lys Glu Thr Glu Phe Leu Arg Leu Lys Arg
             70                  75                  80 aca aga ctt gga ttg gaa gat ttt gag tcc tta aaa gta ata ggc aga        886
Thr Arg Leu Gly Leu Glu Asp Phe Glu Ser Leu Lys Val Ile Gly Arg
                 85                  90                  95 gga gca ttt ggt gag gta cgg ctt gtt cag aag aaa gat acg gga cat        934
Gly Ala Phe Gly Glu Val Arg Leu Val Gln Lys Lys Asp Thr Gly His
             100                 105                 110 gtg tat gca atg aaa ata ctc cgt aaa gca gat atg ctt gaa aaa gag        982
Val Tyr Ala Met Lys Ile Leu Arg Lys Ala Asp Met Leu Glu Lys Glu
     115                 120                 125 cag gtt ggc cac att cgt gcg gag cgt gac att cta gtg gag gca gac       1030
Gln Val Gly His Ile Arg Ala Glu Arg Asp Ile Leu Val Glu Ala Asp
130                 135                 140                 145 agt ttg tgg gtt gtg aaa atg ttc tat agt ttt cag gat aag cta aac       1078
Ser Leu Trp Val Val Lys Met Phe Tyr Ser Phe Gln Asp Lys Leu Asn
                 150                 155                 160 ctc tac cta atc atg gag ttc ctg cct gga ggg gac atg atg acc ttg       1126
Leu Tyr Leu Ile Met Glu Phe Leu Pro Gly Gly Asp Met Met Thr Leu
             165                 170                 175 ttg atg aaa aaa gac act ctg aca gaa gag gag act cag ttt tat ata       1174
Leu Met Lys Lys Asp Thr Leu Thr Glu Glu Glu Thr Gln Phe Tyr Ile
         180                 185                 190 gca gaa aca gta tta gcc ata gac tct att cac caa ctt gga ttc atc       1222
Ala Glu Thr Val Leu Ala Ile Asp Ser Ile His Gln Leu Gly Phe Ile
     195                 200                 205 cac aga gac atc aaa cca gac aac ctt ctt ttg gac agc aag ggc cat       1270
His Arg Asp Ile Lys Pro Asp Asn Leu Leu Leu Asp Ser Lys Gly His
210                 215                 220                 225 gtg aaa ctt tct gac ttt ggt ctt tgc aca gga ctg aaa aaa gca cat       1318
Val Lys Leu Ser Asp Phe Gly Leu Cys Thr Gly Leu Lys Lys Ala His
                 230                 235                 240 agg aca gaa ttt tat agg aat ctg aac cac agc ctc ccc agt gat ttc       1366
Arg Thr Glu Phe Tyr Arg Asn Leu Asn His Ser Leu Pro Ser Asp Phe
             245                 250                 255 act ttc cag aac atg aat tcc aaa agg aaa gca gaa acc tgg aaa aga       1414
Thr Phe Gln Asn Met Asn Ser Lys Arg Lys Ala Glu Thr Trp Lys Arg
         260                 265                 270 aat aga cgt cag cta gcc ttc tcc aca gta ggc act cct gac tac att       1462
Asn Arg Arg Gln Leu Ala Phe Ser Thr Val Gly Thr Pro Asp Tyr Ile
     275                 280                 285 gct cct gag gtg ttc atg cag acc ggg tac aac aag ctc tgt gat tgg       1510
Ala Pro Glu Val Phe Met Gln Thr Gly Tyr Asn Lys Leu Cys Asp Trp
290                 295                 300                 305 tgg tcg ctt ggg gtg atc atg tat gag atg ctc atc ggc tac cca cct       1558
Trp Ser Leu Gly Val Ile Met Tyr Glu Met Leu Ile Gly Tyr Pro Pro
                 310                 315                 320 ttc tgt tct gag acc cct caa gag aca tat aag aag gtg atg aac tgg       1606
Phe Cys Ser Glu Thr Pro Gln Glu Thr Tyr Lys Lys Val Met Asn Trp
             325                 330                 335 aaa gaa act ttg act ttt cct cca gaa gtt ccc atc tct gag aaa gcc       1654
Lys Glu Thr Leu Thr Phe Pro Pro Glu Val Pro Ile Ser Glu Lys Ala
         340                 345                 350 aag gat cta att ttg agg ttc tgc tgt gaa tgg gaa cat aga att gga       1702
Lys Asp Leu Ile Leu Arg Phe Cys Cys Glu Trp Glu His Arg Ile Gly
     355                 360                 365
```

```
gct cct gga gtt gag gaa ata aaa agt aac tct ttt ttt gaa ggc gtt    1750
Ala Pro Gly Val Glu Glu Ile Lys Ser Asn Ser Phe Phe Glu Gly Val
370                 375                 380                 385 gac tgg gaa cat atc aga gag aga cct gct gca ata tct att gaa atc    1798
Asp Trp Glu His Ile Arg Glu Arg Pro Ala Ala Ile Ser Ile Glu Ile
                390                 395                 400 aaa agc att gat gat acc tca aac ttc gat gag ttt cca gaa tct gat    1846
Lys Ser Ile Asp Asp Thr Ser Asn Phe Asp Glu Phe Pro Glu Ser Asp
            405                 410                 415 att ctt aag cca aca gtg gcc aca agt aat cat cct gag act gac tac    1894
Ile Leu Lys Pro Thr Val Ala Thr Ser Asn His Pro Glu Thr Asp Tyr
        420                 425                 430 aag aac aaa gac tgg gtc ttc atc aat tac acg tac aag cgc ttt gag    1942
Lys Asn Lys Asp Trp Val Phe Ile Asn Tyr Thr Tyr Lys Arg Phe Glu
    435                 440                 445 ggc ctg act gca agg ggg gca ata cct tcc tac atg aaa gca gca aaa    1990
Gly Leu Thr Ala Arg Gly Ala Ile Pro Ser Tyr Met Lys Ala Ala Lys
450                 455                 460                 465 tagtactctt gccacggaat cctatgtgga gcagagttct ttgtataaca tcatgctttt    2050
cctctcacac tcttgaagag cttccaagaa gttgatggaa cccaccaata tgtcatagta    2110
aagtctcctg aaatgtggta gtaagaggat tttcttccat aatgcatctg aaaaactgta    2170
aacaaagaca accatttcta ctacgtcggc cataaacagc tatcctgctt tggaagagaa    2230
gcatcatgag ccaatttgat aggtgtttta aaaataactt gagttttcct aagttcatca    2290
gaatgaaggg gaaaaacagc catcatccaa cattattgag attgtcgtgt atagtcatcg    2350
aatatcagcc agttcctgta attttgtgac acgctctctg ccaagcccac caagtatttc    2410
ctttatagct aaaagttcca tagtactaag gaaataaagc aataaagaca gtctcagcag    2470
ccaggattct ggctgaagga aatgatccgc caccctgagg gtggtgatgg tagtttctac    2530
ccatacctca gcctcaggcg agtggcttat agcctccatt catggtgcac tttatttatg    2590
gtactaagat aaagactgtc aatccattga tttatctcct cctgtccccc atctaaaata    2650
cccatgctgc ttttctgagt gttgatgggg gttaccagct tgatccactg ttgctcttag    2710
aaggcccaga aagtctttgg gcattgcaag aaatcccgaa ttatgtggaa accctcact    2770 ttctcttcac ggctgtacca gaaaatccct aagacagatc ttgccgtgga ctagcaatac    2830
ctgcaagtgc tgccaatggg aactcaattt attcctggga acctaacgag gagagcccag    2890
gcctaggcag gaggcctgga accctcttgg ctaaggtgct gttcctgttc ctgcaaggtc    2950
tccagaaccc ctttggaaat ggtgaaggaa ccagcccaat agaagtacag agccagctga    3010
cggaattc                                                            3018

<210> SEQ ID NO 7
<211> LENGTH: 465
<212> TYPE: PRT
<213> ORGANISM: Homo sapiens

<400> SEQUENCE: 7

Met Ala Met Thr Gly Ser Thr Pro Cys Ser Ser Met Ser Asn His Thr
1               5                   10                  15

Lys Glu Arg Val Thr Met Thr Lys Val Thr Leu Glu Asn Phe Tyr Ser
            20                  25                  30

Asn Leu Ile Ala Gln His Glu Glu Arg Glu Met Arg Gln Lys Lys Leu
        35                  40                  45

Glu Lys Val Met Glu Glu Glu Gly Leu Lys Asp Glu Glu Lys Arg Leu
    50                  55                  60
```

-continued

```
Arg Arg Ser Ala His Ala Arg Lys Glu Thr Glu Phe Leu Arg Leu Lys
 65                  70                  75                  80

Arg Thr Arg Leu Gly Leu Glu Asp Phe Glu Ser Leu Lys Val Ile Gly
                 85                  90                  95

Arg Gly Ala Phe Gly Glu Val Arg Leu Val Gln Lys Lys Asp Thr Gly
                100                 105                 110

His Val Tyr Ala Met Lys Ile Leu Arg Lys Ala Asp Met Leu Glu Lys
            115                 120                 125

Glu Gln Val Gly His Ile Arg Ala Glu Arg Asp Ile Leu Val Glu Ala
130                 135                 140

Asp Ser Leu Trp Val Val Lys Met Phe Tyr Ser Phe Gln Asp Lys Leu
145                 150                 155                 160

Asn Leu Tyr Leu Ile Met Glu Phe Leu Pro Gly Gly Asp Met Met Thr
                165                 170                 175

Leu Leu Met Lys Lys Asp Thr Leu Thr Glu Glu Thr Gln Phe Tyr
                180                 185                 190

Ile Ala Glu Thr Val Leu Ala Ile Asp Ser Ile His Gln Leu Gly Phe
            195                 200                 205

Ile His Arg Asp Ile Lys Pro Asp Asn Leu Leu Leu Asp Ser Lys Gly
210                 215                 220

His Val Lys Leu Ser Asp Phe Gly Leu Cys Thr Gly Leu Lys Lys Ala
225                 230                 235                 240

His Arg Thr Glu Phe Tyr Arg Asn Leu Asn His Ser Leu Pro Ser Asp
                245                 250                 255

Phe Thr Phe Gln Asn Met Asn Ser Lys Arg Lys Ala Glu Thr Trp Lys
                260                 265                 270

Arg Asn Arg Arg Gln Leu Ala Phe Ser Thr Val Gly Thr Pro Asp Tyr
                275                 280                 285

Ile Ala Pro Glu Val Phe Met Gln Thr Gly Tyr Asn Lys Leu Cys Asp
290                 295                 300

Trp Trp Ser Leu Gly Val Ile Met Tyr Glu Met Leu Ile Gly Tyr Pro
305                 310                 315                 320

Pro Phe Cys Ser Glu Thr Pro Gln Glu Thr Tyr Lys Lys Val Met Asn
                325                 330                 335

Trp Lys Glu Thr Leu Thr Phe Pro Pro Glu Val Pro Ile Ser Glu Lys
                340                 345                 350

Ala Lys Asp Leu Ile Leu Arg Phe Cys Cys Glu Trp Glu His Arg Ile
            355                 360                 365

Gly Ala Pro Gly Val Glu Glu Ile Lys Ser Asn Ser Phe Phe Glu Gly
370                 375                 380

Val Asp Trp Glu His Ile Arg Glu Arg Pro Ala Ala Ile Ser Ile Glu
385                 390                 395                 400

Ile Lys Ser Ile Asp Asp Thr Ser Asn Phe Asp Glu Phe Pro Glu Ser
                405                 410                 415

Asp Ile Leu Lys Pro Thr Val Ala Thr Ser Asn His Pro Glu Thr Asp
            420                 425                 430

Tyr Lys Asn Lys Asp Trp Val Phe Ile Asn Tyr Thr Tyr Lys Arg Phe
            435                 440                 445

Glu Gly Leu Thr Ala Arg Gly Ala Ile Pro Ser Tyr Met Lys Ala Ala
            450                 455                 460

Lys
465
```

```
<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: PCR Primer

<400> SEQUENCE: 8
aaggatccat ggcaatgaca ggctc                                           25

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: PCR Primer

<400> SEQUENCE: 9
tttctgcttt ccttttg                                                    17

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 10
gttttcccag tcacgacgtt gtaaaacg                                        28

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 11
ggagtattgc cattgcat                                                   18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 12
atgcaatggc aatactcc                                                   18

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 13
gagtcgtttc tcctcatc                                                   18

<210> SEQ ID NO 14
<211> LENGTH: 19
<212> TYPE: DNA
<213> ORGANISM: Artificial Sequence
<220> FEATURE:
<223> OTHER INFORMATION: Description of Artificial Sequence: PCR Primer
```

```
<400> SEQUENCE: 14
acaagacttg gattggaag                                                      19

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: PCR Primer

<400> SEQUENCE: 15
tctagctagc tgggaattca tgttctg                                             27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: PCR Primer

<400> SEQUENCE: 16
catgccatgg gattggaaga ttttgag                                             27

<210> SEQ ID NO 17
<211> LENGTH: 12
<212> TYPE: PRT
<213> ORGANISM: Homo sapiens

<400> SEQUENCE: 17

Lys Arg Lys Ala Glu Thr Trp Lys Arg Asn Arg Arg
 1               5                  10

<210> SEQ ID NO 18
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Predicted carboxy terminus of human Ndr

<400> SEQUENCE: 18

Thr Ala Arg Gly Ala Ile Pro Ser Tyr Met Lys Ala Ala Lys
 1               5                  10
```

NUCLEIC ACIDS ENCODING NUCLEAR DBF2-RELATED (NDR) KINASES

This is a divisional application of U.S. application Ser. No. 08/860,150, filed Jun. 19, 1997 now U.S. Pat. No. 5,981,205 issued on Nov. 9, 1999. Ser. No. 08/865,150 is a national stage application of PCT/EB95/05052 filed Dec. 20, 1995.

The current invention describes the identification of a novel widely-expressed human and *D. melanogaster* serine/threonine protein kinase (designated nuclear, Dbf2-related kinase, or Ndr; previously referred to as Pun kinase) and the use of this kinase for the identification of modulators thereof. The kinase is a nuclear protein and contains a short basic peptide, KRKAETWKRNRR, responsible for nuclear accumulation.

Reversible protein phosphorylation is a major mechanism for the co-ordinated control of many fundamental cellular functions in eukaryotic organisms, including metabolism, growth, and differentiation. The phosphorylation status, and consequently the activity, of specific target proteins is regulated by the opposing actions of protein kinases and protein phosphatases. Generally, these enzymes are specific either for serine/threonine or for tyrosine phosphoacceptors, although some dual specificity kinases and phosphatases have also been described. The importance of phosphorylation cascades is reflected by the finding that many kinases, phosphatases, and the signal transduction pathways in which they participate have been highly conserved during the course of evolution. In recent years, interest has focused on the role of protein phosphorylation in the control of the cell cycle; a number of cellular proto-oncogenes encode members of the serine/threonine kinase family and it has become increasingly clear that certain serine/threonine kinases function as key components of the cell cycle regulatory network. Therefore, the complete delineation of these pathways is an important aim for the understanding of oncogenesis and tumour progression.

The *C. elegans* expressed sequence tags (ESTs) cm11b7 and cm11b8 are overlapping cDNA clones which were originally described as worm homologues of the human kinase RAC/Akt (RAC-PK) and the *S. cerevisiae* cell cycle regulated kinase Dbf2 (Waterston et al., (1992) Nat. Genet. 1, 114–123). By complete sequencing of the clones, it has been determined that this homology assignment is incorrect Surprisingly it has been found that a novel kinase, distinct from RAC-PK and Dbf2, which is highly homologous to cm11b8 can be isolated from human and *D. melanogaster* sources. This kinase, Ndr, binds to calmodulin in a calcium-dependent manner. The gene encoding Ndr is located on human chromosome 6, between 6p21.2 and 6p21.31, a region of chromosome 6 which contains the major histocompatibility complex (MHC) class 1 genes. It has also been found that DNA encoding Ndr can be overexpressed when comprised in a suitable expression system, and that the protein sequence contains a short fragment that is responsible for the nuclear localisation of proteins.

SUMMARY OF THE INVENTION

In a first aspect of the present invention, we provide Ndr protein kinase, as well as homologues and derivatives thereof. Moreover, the invention relates to a nuclear localisation sequence derived from Ndr, and the use of Ndr for the modulation of calcium signalling.

DETAILED DESCRIPTION OF THE INVENTION

By conducting sequencing and homology studies using *C. elegans* cm11b7 and cm11b8 clones, we have determined that they represent a new protein kinase rather than a worm homologue of RAC-PK. The current invention concerns novel protein kinases comprising the amino acid sequence as given in SEQ ID NO:2 and SEQ ID NO:7 or a homologue thereof. The kinases of the invention are designated Ndr.

Ndr and its homologues are polypeptides which share sufficient similarities for the skilled person to determine that they share homology of origin or function with the Ndr protein kinases as represented by human and Drosophila Ndr. The invention includes all species homologues of Ndr. Human and dDrosophila Ndr, represented in SEQ ID No. 7 and SEQ ID No. 2, are species homologues. Species homologues from other organisms may be isolated according to the methods set out herein, which are conventional. Moreover, suitable alternative methods are known to those of skill in the art and may be found in the literature. Species homologues of Ndr may be considered derivatives of the polypeptide sequences set out herein. The invention does not, however, comprise the sequences of *C. elegans* cm11b7 and cm11b8 per se.

In a preferred case, homology is used herein to refer to sequence identity. Thus, homologues are also polypeptides which share a certain amount of sequence identity with the Ndr protein kinases as herein described. Preferably, the sequence identity is 50% or more, more preferably 60% or more and most preferably 75% or more. Human and Drosophila Ndr sequences share 68% sequence identity. Dbf2, on the other hand, possesses only 32% overall amino acid identity with human Ndr, suggesting that Dbf2 is related to Ndr, but that the two are not species homologues.

Where amino acid residues in members of the Ndr protein kinase family are not identical, the may be similar, wherein the substitutions present are preferably conservative substitutions or alterations which do not alter the structure/function relationship of the domains of the kinase. Thus, the sequence similarity between human and Drosophila Ndr is about 80%.

Derivatives of said polypeptides, which form part of the present invention, also comprise mutants and fragments of Ndr. A mutant is a polypeptide that has, for example, one or more amino acid deletions, additions or substitutions, that is devoid of a certain domain or that is connected to another polypeptide, e.g., in form of a fusion protein. A mutant according to the invention still reacts comparably to the natural Ndr, e.g., in respect to the enzymatic activity or specificity; thus, although its overall activity may be modulated or altered in minor ways, Ndr and mutants thereof are essentially functionally equivalent Fragments of Ndr comprise the Ndr polypeptide, or a mutant thereof, in which a substantial part of the polypeptide has been removed. Fragments of Ndr may have a substantially different activity to natural Ndr. Thus, Ndr fragments may comprise an individual kinase domain thereof, or a subset of the kinase domains of natural Ndr, or the calmodulin binding domain, the nuclear localisation signal and the like.

For instance, it has been found that the amino acids 265–276 (KRKAETWKRNRR) of the human Ndr code for a nuclear localisation signal. Accordingly, the current invention also comprises a fragment of Ndr acting as a nuclear localisation signal and having the amino acid sequence KRKAETWKRNRR; and to a functional derivative thereof having the same nuclear localisation effect and to a DNA coding for this nuclear localisation signal. Also embraced is the use of this sequence for the construction of a polypeptide that is localised mainly in the nucleus.

Moreover, Ndr is found to contain all of the 12 protein kinase catalytic subdomains identified by Hanks and Quinn (Meth. Enzymol. (1991) 200, 38–62). Of these, the presence of subdomains VIb and VIII suggest that Ndr is a serine/threonine kinase. Thus, the invention includes any subset of the kinase domains of Ndr, especially the serine/threonine kinase domains.

If the polypeptide of the invention is expressed in form of a fusion protein, the fused polypeptides may be connected directly or by a spacer. It is for example possible to insert, if not already naturally present, a region that can be specifically recognised and cleaved chemically or enzymatically. Examples for selective cleaving reagents or enzymes are CNBr, V8 protease, trypsin, thrombin, factor X, peptidase yscα and yscF. Methods for the construction of fusion proteins, mutations or fragments by recombinant or chemical techniques are known in the art.

Isolation

The polypeptide of the invention can be isolated from natural sources by conventional means, from tissues or from cultured cells. During the isolation conventional additives like protein stabilisers, inhibitors of proteinases and the like may be added. For example, when the polypeptide is isolated from tissue culture, the first step consists usually in lysing the cells or, in the case where the polypeptide is secreted into the medium, in separating the cells from the culture fluid by means of centrifugation. In the presence of additional proteins and impurities, the resulting supernatant can be enriched for the polypeptide of the invention, e.g., by treatment with polyethyleneimine so as to remove most of the non-proteinaceous material, and precipitation of proteins by saturating the solution with ammonium sulphate or the like. Host proteins, if present, can also be precipitated by means of acidification with acetic acid and other conventional means. Other purification steps may include, for example, removing the lectins, desalination, chromatographic processes, such as ion exchange chromatography, gel filtration chromatography, partition chromatography, HPLC, reversed phase HPLC and the like. The separation of the constituents of the mixture is also effected by dialysis, according to charge by means of gel electrophoresis or carrier-free electrophoresis, according to molecular size by means of a suitable Sephadex column, gel-permeation or ultrafiltration, by affinity chromatography, or by other processes, especially those known from the literature.

The polypeptide, and especially its derivatives, may be obtained by synthetic means rather than derived from natural sources. Thus, using the information contained herein, Ndr polypeptide may be synthesised using commercially available protein synthesisers or even ordered from a commercial peptide synthesis service. Synthesised derivatives of Ndr may comprise any desired sequence modifications, including the use of altered amino acid residues or the addition of heterologous groups or side-chains to the polypeptide.

Use of the polypeptide of the invention

Kinases such as Ndr are known to be involved in signal transduction within cells. This involvement makes kinases targets for agents which seek to obtain a biological effect by modulating a signalling pathway. Typically, modulation of a signalling pathway will alter the response of a cell to a particular stimulus. For example, the effect of hormones may be modulated by targeting the kinases involved in signal transduction from the hormone receptor to the biological effectors, which are typically regulators of gene expression.

Calmodulin is the major calcium ion binding protein in the cell and is involved in calcium-mediated effects. It has been determined that Ndr binds to calmodulin in a calcium dependent manner, such that the binding of calmodulin to Ndr is fully reversible by calcium sequestration. The activity of Ndr is regulated by calmodulin.

Accordingly, there is provided a method for influencing the effect of calmodulin on a cell comprising modulating the response of Ndr thereto. Preferably, the method comprises bringing the cell into contact with an activator or an inhibitor of Ndr. Activators and inhibitors, which include Ndr mimics and are referred to collectively as modulators, may interact with Ndr at or near the calmodulin binding site, thereby influencing the effect of calmodulin on Ndr activity. Alternatively, modulators may act at a site remote from the calmodulin binding site, activating or repressing the activity of Ndr by other means. For example, the modulators may influence the ability of Ndr to phosphorylate its substrate (s), potentially by modifying the three-dimensional configuration of Ndr, for example to influence the binding energy between Ndr and its substrate(s), or influence the subcellular localisation of Ndr, its interaction with associated cellular factors, and the like. Still further modulators may influence the activity of Ndr by targeting the factors and substrates which interact with Ndr, rather than Ndr itself.

The invention also provides a method of treating a disease associated with an anomaly of calmodulin response comprising administering to a subject a pharmaceutically effective amount of an Ndr modulator. Ndr modulators for use in such a method may be formulated according to conventional methodology, depending on the exact nature of the modulator, and will typically comprise the modulator or a precursor thereof in association with a biologically acceptable carrier.

In certain circumstances, if it can be determined that the deficiency in calmodulin response is caused by an anomaly associated directly with Ndr, the Ndr modulator may take the form of Ndr itself, such that the condition is treated by administering exogenous Ndr. In this case, Ndr may be formulated with agents acceptable for pharmaceutical administration of proteinaceous agents and delivered to the subject by acceptable routes, such as via liposomes.

Moreover, Ndr or a modulator thereof may be provided to the cell in the form of a nucleic acid which can be translated in the cell to provide Ndr or a modulator thereof in situ. Thus, the invention includes methods of gene therapy comprising administering to a cell a nucleic acid encoding Ndr or a modulator thereof such that the nucleic acid is expressed within the cell to produce Ndr or its modulator. The invention includes the administration of nucleic acids which possess an Ndr modulating activity per se, such as antisense oligonucleotides which target Ndr itself or a molecule which influences the activity of Ndr.

Ndr also may be used directly for binding studies and in the screening of possible modulators thereof. For binding studies, the polypeptide of the invention may be, for example, immobilised on a solid carrier like a microtiter plate or beads; or may bear one or more identifiable marker like biotin or a radioactive, fluorescent or chemiluminescent group. In a preferred embodiment of the present invention, Ndr is used in a method for screening potential modulators of Ndr activity. In such a method, the activity of Ndr is monitored by suitable means, for example by a functional assay which measures the kinase activity of Ndr. Kinase activity assays are known in the art. Therefore, the invention provides a method for screening a compound which is a potential modulator of Ndr activity comprising the steps of:

a) incubating a kinase according to claim 1 with the compound;

b) determining the compound-induced modulation in the activity of the kinase, an alteration of the activity in the presence of the compound being indicative of a functional interaction between the compound and the kinase.

Incubation conditions will vary according to the precise method used to detect the interaction between the kinase and the screened compound. In the case of transcription activation detection systems such as the yeast two-hybrid system, incubation conditions are suitable for gene transcription, such as those prevailing inside a living cell. Other detection systems, however, will require different incubation conditions. For example, if the detection of interaction is based on relative affinity in a chromatographic assay, for example as is known in affinity chromatography, conditions will be adjusted to promote binding and then gradually altered, such that the point at which the screened compound no longer binds to Ndr may be determined.

Incubation according to the invention may be achieved by a number of means, but the basic requirement is for the kinase or a fragment thereof and the screened compound to be able to come into contact with each other. This may be achieved by admixing Ndr or a fragment thereof and the compound, or by producing them in situ, such as by expression of nucleic acids encoding them. Where Ndr or the Ndr fragment and/or the compound are in the form of fusions with other polypeptides, they may be expressed as such in situ.

Preferably, the method of the invention is based on a two-hybrid system. Such systems detect specific protein-:protein interactions by exploiting transcriptional activators having separable DNA-binding and transcription activating domains, such as the yeast GAL4 activator. A reporter gene is operatively linked to an element responsive to the transcriptional activator being used, and exposed to Ndr or a fragment thereof and the compound to be screened, one of which is complexed to the transcription activating domain of the transcriptional activator and the other of which is joined to the DNA binding domain thereof. If there is a specific interaction between Ndr or a fragment thereof and the compound, the DNA binding and transcription activating domains of the transcriptional activator will be brought into juxtaposition and transcription from the reporter gene will be activated.

Alternatively, the detection may be based on observed binding between Ndr or a fragment thereof, such as its nuclear localisation signal or its catalytic domains, and the screened compound, or a fragment thereof. For example, the interaction between Ndr and a potential modulator may be assayed by monitoring the interaction of a portion of the modulator, known to be involved in modulation events, with Ndr.

Ndr or a fragment thereof may be used to screen for compounds which bind thereto by incubating it with the compound to be screened and subsequently "pulling down" Ndr complexes with an Ndr-specific antibody. Antibodies suitable for immunoprecipitation or immuno-affinity chromatography may be prepared according to conventional techniques, known to those of ordinary skill in the art, and may be monoclonal or polyclonal in nature. After the Ndr-compound complex has been isolated by affinity, the compound may be dissociated from the Ndr antibody and characterised by conventional techniques.

The interaction of Ndr or a fragment thereof with the screened compound may also be observed indirectly. For example, an inhibitor or activator of Ndr function may be detected by observing the effects of Ndr on a substrate in the presence or absence of the compound.

The activity of Ndr or a catalytic domain thereof may be assessed by means of a kinase activity assay, employing a substrate for the kinase. For example, autophosphorylation may be measured, in accordance with established assay procedures. Exogenous physiological substrates may also be used.

The invention further comprises the use of Ndr or a fragment thereof in a screening system. The screening system is preferably used to screen for compounds which are modulators of calmodulin activity, particularly where that activity is related to cell proliferation.

Kits useful for screening such compounds may be prepared, and will comprise essentially Ndr or a fragment thereof together with means for detecting an interaction between Ndr and the screened compound. Preferably, therefore, the screening kit comprises one of the detection systems set forth hereinbefore.

Ndr for use in kits according to the invention may be provided in the form of a protein, for example in solution, suspension or lyophilised, or in the form of a nucleic acid sequence permitting the production of Ndr or a fragment thereof in an expression system, optionally in situ. Preferably, the nucleic acid encoding Ndr or a fragment thereof encodes it in the form of a fusion protein, for example a GST fusion.

In a still further embodiment, the invention provides a compound which interacts directly or indirectly with Ndr or a fragment thereof. Such a compound may be inorganic or organic, for example an antibiotic, and is preferably a proteinaceous compound involved in intracellular signalling.

Compounds according to the invention may be identified by screening using the techniques described hereinbefore, and prepared by extraction from natural sources according to established procedures, or by synthesis, especially in the case of low molecular weight chemical compounds. Proteinaceous compounds may be prepared by expression in recombinant expression systems, for example a baculovirus system, or in a bacterial system. Proteinaceous compounds are mainly useful for research into the function of signalling pathways, although they may have a therapeutic application.

Low molecular weight compounds, on the other hand, are preferably produced by chemical synthesis according to established procedures. They are primarily indicated as therapeutic agents. Low molecular weight compounds and organic compounds in general may be useful as antiproliferative agents.

Preferably, modulators of Ndr activity are modulators of calcium response in the cell. Thus, the invention provides a method for screening potential modulators of calcium response comprising assaying the effect of such modulators on the activity of Ndr, an effect on said activity being indicative of potential in the compound as a calcium response modulator.

In order to increase the understanding of Ndr activity and potentially improve Ndr modulators, isolated polypeptide can be used to identify the 3-dimensional structure of the whole protein or at least of the areas responsible for the enzymatic activity and regulation. Conventional methods for the identification of the 3-dimensional structure are, for example, X-ray studies or NMR studies. The data received with these or comparable methods may be used directly or indirectly for the identification or improvement of modulators of Ndr. A commonly used method in this respect is, for example, computer aided drug design or molecular modelling.

A further embodiment of the invention concerns the modulator identified with the polypeptide of the invention, or with the aid of the 3-dimensional structure derived therefrom, for use in a method of treatment.

Plasmids and DNA

A further embodiment of the current invention is a nucleic acid encoding Ndr. This nucleic acid DNA may also contain one or more introns.

Nucleic acids encoding Ndr include nucleic acids which do not encode the whole of the Ndr polypeptide as herein disclosed. Thus, the invention provides fragments of the entire Ndr coding sequence. Such fragments preferably encode fragments of Ndr, or derivatives thereof, as hereinbefore defined. A fragment of the nucleic acid can be used, for example, as a hybridisation probe to identify DNA that codes for a related protein or can be used to screen for the transcription products of the protein of the invention in certain tissues. Suitable fragments are preferably larger than 20 nucleotides.

The DNA coding for the protein of the invention, as described above, may be comprised in a nucleic acid expression cassette comprising a promoter operably linked to a nucleic acid as defined above and optionally to transcription termination signals.

The promoter can be of almost any origin. It is for example possible to use a tightly regulated promoter or the promoter that is naturally adjacent to the Ndr gene. Preferred are promoters that are active in the chosen host cells like the SV40, tac, β-actin, metallothionein, T7, polyhedrin and cytomegalovirus promoter.

A DNA sequence containing the transcription termination signals is preferably the 3' flanking sequence of a gene that contains proper signals for transcription termination and polyadenylation for the desired host. Suitable signals are, for example, the polyadenylation signal of the human growth hormone, of the DHFR gene and of the rabbit β-globin gene.

A preferred DNA coding for the polypeptide of the invention is depicted in SEQ ID NO: 1 and SEQ ID NO:6.

It is also possible to use a polypeptide expression cassette additionally containing a signal sequence, that causes the protein produced to be secreted into the medium. Suitable signal sequences are known in the art. Accordingly, in these kinds of expression cassettes a promoter is operably linked to a first DNA sequence encoding a signal peptide linked in the proper reading frame to a second DNA sequence coding for the polypeptide of the invention, and a DNA sequence containing transcription termination signals.

The promoter, the DNA sequence coding for the protein of the invention and the DNA sequence containing transcription termination signals are operably linked to each other, i.e., they are juxtaposed in such a manner that their normal functions are maintained. The array is such that the promoter effects proper expression of the structural gene and the transcription termination signals effect proper termination of transcription and polyadenylation. The junction of these sequences may, for example, be effected by means of synthetic oligodeoxynucleotide linkers carrying the recognition sequence of an endonuclease.

The expression cassettes according to the invention may be inserted into the desired host in form of a stable plasmid or directly into the chromosome, of which the latter is preferred.

It is likewise possible that the expression plasmids according to the invention include one or more, especially one or two, selective genetic markers for the host used for the construction, amplification and test of the plasmid, such a marker and an origin of replication for a bacterial host, especially *Escherichia coli*.

As to the selective gene markers, any marker gene can be used which facilitates the selection for transformants due to the phenotypic expression of the marker gene. Suitable markers are, for example, those expressing antibiotic resistance or, in the case of auxotrophic host mutants, genes which complement host lesions. Corresponding genes confer, for example, resistance to the antibiotics tetracycline, ampicillin, G418, hygromycin or bleomycin or provide for prototrophy in an auxotrophic mutant, for example the URA3, LEU2, LYS2, HIS3 or TRP1 gene.

As the amplification of the expression plasmids is usually done in a prokaryote, such as *E. coli*, a replication origin are included advantageously. These can be obtained from corresponding prokaryotic plasmids, for example *E. coli* plasmids, such as pBluescript® pBR322, pTZ18R, or a pUC plasmid, for example pUC18 or pUC19, which contain both prokaryotic, e.g. *E. coli*, replication origin and genetic marker conferring resistance to antibiotics, such as ampicillin and tetracycline.

Apart from the polypeptide expression cassette, replication origin(s) and genetic marker(s) the expression plasmids according to the invention can contain optionally additional expression cassettes, such as 1 to 3 additional polypeptide expression cassettes, which may be the same or different.

The expression plasmids according to the invention are prepared by methods known in the art, for example by linking the polypeptide expression cassette, the DNA fragments containing selective genetic markers for the host used in the test and optionally for a bacterial host, the origin(s) of replication, and the optionally additional polypeptide expression cassettes in the predetermined order using conventional chemical or biological in vitro synthesis procedures. Preferentially, the plasmids are constructed and prepared using recombinant DNA techniques. For the preparation by recombinant DNA techniques suitable DNA fragments are ligated in vitro in conventional manner. The ligation mixture is then transformed into a suitable prokaryotic or eukaryotic host depending on the nature of the regulatory elements used, and a transformant containing the desired vector is selected according to conventional procedures. The plasmids can be multiplicated by means of the transformed hosts and can be isolated in conventional manner. The choice of the host depends on the regulatory sequences located on the vector. For the construction and multiplication of the vector a prokaryotic host, e.g. *E. coli*, is preferred.

Hosts, transfection and culturing

A suitable host for the production of the polypeptide of the invention is a eukaryotic or prokaryotic cell, for example a mammalian, nematode, insect, yeast or bacterial cell.

The suitable host, as defined above, can be transfected by the standard methods in genetic engineering, for example with the aid of a virus, lipid vesicles, particle gun or electroporation. To increase the amount of protein produced, it is advantageous to use a high copy plasmid or the plasmid DNA is integrated into the genome in several copies. The latter can be achieved, for example, through applying a selective stress, e.g., using methotrexate.

The transfected host cells can be cultured by standard methods in cell culture.

Accordingly, a further embodiment of the current invention concerns a process for the production of the polypeptide of the invention comprising culturing a transfected host as defined above and isolating the polypeptide produced thereby.

The DNA coding for the polypeptide of the invention may be used also for the design of antisense RNA or DNA to inhibit the translation of Ndr in the organism, e.g., in order to influence effects that may be caused by an overexpression or deregulation of the natural Ndr, as well as to target factors which themselves influence Ndr.

A further embodiment of the invention concerns antibodies that are specific for Ndr, especially human Ndr. Such antibodies may be useful for identifying or isolating Ndr, for example by immunostaining or immunoseparation, or for disrupting Ndr activity in vivo or in vitro.

Ndr-specific antibodies may be prepared according to techniques known in the art. In order to prepare a polyclonal serum, for example, an antigenic portion of Ndr, consisting of a peptide derived therefrom, such as a C-terminal peptide, or even the whole kinase, optionally in the presence of an adjuvant or conjugated to an immunostimulatory agent such as keyhole limpet haemocyanin, is injected into a mammal such as a mouse or a rabbit and antibodies are recovered therefrom by affinity purification using a solid-phase bound kinase or antigenic portion thereof. Monoclonal antibodies may be prepared according to similar established procedures.

The invention is further described, for the purposes of illustration only, in the following examples.

EXAMPLES

Standard methods in genetic engineering like random priming, subcloning, sequencing, cleavage with restriction enzymes, gel purification, ligations, transformation and annealing are carried out essentially as described in Sambrook et al., Molecular Cloning: A laboratory manual, $2^{nd}$ Edn. Cold Spring Harbor Laboratory Press, Cold Spring Harbor N.Y., 1989.

Abbreviations:

| | |
|---|---|
| bp | base pair |
| C. elegans | Caenorhabditis elegans |
| D. melanogaster | Drosophila melanogaster |
| DMEM | Dulbecco's Modified Eagle's Medium |
| FCS | Fetal Calf Serum |
| IPTG | Isopropyl β-D-thiogalactopyranoside |
| nt | nucleotide |
| nts | nucleotides |
| PBS | phosphate buffered saline |
| pI | isoelectric point |
| SDS | sodium dodecyl sulphate |
| SSC | 0.15 M NaCl/15 mM Na citrate, pH 7.0 |

Example 1

Identification of Drosophila Ndr

The C. elegans EST clone cm11b8 (Waterston et al., Nature Genet, (1992), 1, 114–123) is radiolabelled by random priming and used to screen a Drosophila embryo cDNA library constructed in λZAPII (Stratagene) at low stringency (Sambrook et al.). This results in the isolation of a 2.1 kb clone SDEpunk-12 (deposited with DSM), which is completely sequenced (SEQ ID No.1) and contains a complete open reading frame of 456 amino acids (SEQ ID No.2).

Example 2

Identification of human Ndr

Degenerated oligonucleotides are designed corresponding to amino acid sequences conserved between C. elegans cm11b8 (SEQ ID NO:3) and Drosophila Ndr (SEQ ID NO:2, from Example 1) for amplification of the human homologue. This amplification is performed via PCR on reverse-transcribed total RNA isolated from HeLa cells by the guanidine isothiocyanate method as described in Sambrook et al. using primers with SEQ ID No. 4 (XbaI-site underlined) and SEQ ID No. 5 (HindIII-Site underlined).

SEQ ID NO 4:
5'- ATCTAGAAARGAIACIGARTAYYTIMGIYTIAA, -3'
SEQ ID NO 5: 5'- AAAAGCTTGGIGCDATRTARTCIG-GIGTICCIAC -3'

The final reaction mix (50 µl) contains 10 mM Tris-HCl, pH 8.3, 50 mM KCl, 2 mM MgCl$_2$, 200 µM each dNTP, 50 pmoles of each primer, 5 µl cDNA and 2.5 units of Taq polymerase. Reactions are cycled 30 times through 95° C. (1 minute), 55° C. (2 minutes), and 72° C. (3 minutes). Following this, 5 µl of the reaction is removed and reamplified as above.

The PCR product is subcloned in pBluescript® (Stratagene), labelled by random priming and used to screen human cDNA libraries derived from fetal brain, fetal retina, placenta and adult heart; each constructed in λZAPII® (Stratagene, see above) following standard protocols (Sambrook et al.). Partial-length clones are found in each of these libraries.

Plasmid rescue is carried out as recommended by the manufacturer (Stratagene). The PCR product and library clones that show positive signals in the screens are fully sequenced on both strands using Sequenase (USB) and custom synthesised primers.

BBZpunk-16b (deposited with DSM) and BBZpunk-3a (deposited with DSM), two clones of the fetal brain λZAPII® cDNA library encompassing a complete open reading for human Ndr, are used to assemble the full-length human Ndr cDNA into the EcoRI site of pBluescript® (Stratagene) using their common XmnI site (nucleotides 1045–1054). A 1.1 kb EcoRI/XmnI fragment of clone BBZpunk-16b and a 0.7 kb XmnI/SacI fragment of clone BBZpunk-3a are ligated together between the EcoRI and SacI sites of pBluescript®. This intermediate plasmid is cut with SacI and ligated with the 1.3 kb SacI/SacI fragment of BBZpunk-3a. The resulting plasmid is designated pBLM-punk The assembled cDNA is excised therefrom with HindIII and XbaI and subcloned into HindIII/XbaI-cut pECE a SV40-based expression vector which is constructed according to the description given in Ellis et al. (Cell (1986), 45, 721–732) to create the plasmid pECE-punk The clone covers a total of 3018 bp, with a single open reading frame extending from nt 566 to nt 1990. The first methionine in the open reading frame is at nts. 596–598. Translation from this methionine gives 465 amino acid polypeptide with a pI of 7.2 and a molecular weight of 54.2 kDa. Alignment of the deduced amino acid sequence with that of Drosophila reveals many highly-conserved regions; the overall amino acid identity between human and Drosophila Ndr is 68%.

The complete human Ndr sequence is depicted in SEQ ID Nos. 6 and 7. Sequences were analysed using the University of Wisconsin GCG software package.

Example 3

Expression of Ndr in human tissues

The 1.7 kb EcoRI fragment of BBZpunk-3a (see example 2) is $^{32}$P-labelled to a specific activity of ~1×10$^9$ cpm/µg by random priming and used to probe a human tissue RNA blot (Clontech) following the manufacturer's recommendations.

The following tissues are tested:

Heart, brain, placenta, lung, liver, skeletal muscle, kidney and pancreas.

After hybridisation the blot is washed to a final stringency of 0.2×SSC/0.1 % SDS (1×SSC =0.15 M NaCl/15 mM Na citrate, pH 7.0) at 60° C. before exposure to Kodak XAR film for 3 weeks at −70° C. with 2 intensifying screens. For quantitation, the blot is analysed with a Phosphorimager® (Molecular Dynamics).

Using this Northern analysis a single 3.9 kb transcript is detected in all tissues analysed. The mRNA is most abundant in kidney, while only a trace amount can be detected in adult brain, with transcript levels varying ~30-fold between kidney and brain. A transcript size of 3.9 kb is consistent with the results of cDNA library screens: during screening, a partial-length cDNA is isolated from a human heart muscle library which is collinear with the fetal brain sequence from nt 1375, and ended in a poly(A) tail 2515 bp downstream of this. Thus, by assembling clones from different libraries a total of 3890 bp of cDNA is recovered. The presence of the Ndr transcript in several cell lines tested by RT-PCR (as described in example 2), and in all human cDNA libraries screened (see example 2), is consistent with the idea that Ndr is a widely (possibly constitutively) expressed enzyme. Taken together with its conservation across divergent eukaryotes, this further implies that Ndr is important in some essential cellular function.

Example 4
Expression of Ndr enzyme activity in bacteria

For the in vitro characterisation of Ndr activity, the human cDNA was isolated from BBZpunk-16b (see example 2) and cloned into the bacterial expression vector pGEX2T (Pharmacia, Smith and Johnson, Gene (1988), 67, 31–40) to generate a glutathione-S-transferase (GST)-Ndr fusion protein. As a negative control, a mutant form of Ndr was generated in which lysine 118 was changed to alanine. Lysine 118 corresponds to the invariant lysine of all protein kinases which contacts the α and β phosphates of ATP, and is essential for catalysis.

Amplifications for mutagenesis are achieved using Pfu polymerase (Stratagene), and all amplified regions are sequenced after subcloning in pBluescript® to confirm the presence of the mutation and the absence of additional mutations. The following mutagenic primers are used:

```
SEQ ID NO:8   5'- AAGGATCCATGGCAATGACAGGCTC    -3'
SEQ ID NO:9   5'- TTTCTGCTTTCCTTTTG            -3'
SEQ ID NO:10  5'- GTTTTCCCAGTCACGACGTTGTAAAACG -3'
SEQ ID NO:11  5'- GGAGTATTGCCATTGCAT           -3'
SEQ ID NO:12  5'- ATACAATGGCAATACTCC           -3'
```

To make the plasmid pGEX2T-punk, the cDNA clone BBZpunk-16b is amplified with primers SEQ ID NO:8 and SEQ ID NO:10. A BamHI/XmnI fragment of the cloned PCR product is ligated together with the 5' XmnI/EcoRI fragment of cDNA clone BBZpunk-3a into BamHI/EcoRI-cut pGEX2T. The resultant plasmid is cut with EcoRI and ligated to the 3' EcoRI fragment of BBZpunk-3a.

To change lysine 118 to alanine, a two-step PCR procedure is used. Plasmid pBLM-punk was amplified using primer pairs SEQ ID NO:8/SEQ ID NO:11 and SEQ ID NO:9/SEQ ID NO:12. The two products are gel purified, denatured, annealed to each other and reamplified using primers SEQ ID NO:8 and SEQ ID NO:9. The secondary PCR product is cut with NcoI and EcoRI and cloned between the corresponding sites in pGEX2T-punk to generate pGEX2T-punkK118A.

In both cases, purification on glutathione-agarose yielded proteins of the expected size (~82 kDa) with a yield of ~0.25 mg per litre of bacteria. About 50% of the purified protein is full-length; minor species migrating at 28–35 kDa are assumed to be degradation products of the fusion proteins, since purification of free GST under identical conditions yielded virtually homogenous protein.

To measure the activity, E. coli-JM109 cells (Clontech) transformed with the appropriate plasmid are grown under standard conditions to mid-log phase then induced with 0.1 mM IPTG overnight at room temperature. Following this, bacteria are harvested, lysed by sonication and fusion proteins purified on glutathione agarose (Sigma) essentially as described in Smith and Johnson, Gene (1988), 67, 31–40. Recombinant proteins are assayed for kinase activity in 20–35 µl 50 mM Tris-HCl, pH 7.5/10 mM $MgCl_2$/1 mM dithiothreitol containing 100 µM [$^{32}$P]-γ-ATP (15–25 µCi). After 30 minutes at 30° C., Laemmli sample buffer (Laemmli et at., Nature (1970) 227, 680) is added and reactions are analysed by 10% SDS-PAGE followed by autoradiography of the dry gel at −70° C. with 2 intensifying screens.

No phosphorylation of non-specific kinase substrates, including histone HI, myelin basic protein, casein and phosvitin can be detected. However, phosphorylation of an ~82 kDa band based on the autophosphorylation of GST-Ndr is consistently observed. Phosphoamino acid analysis of in vitro autophosphorylated Ndr (carried out as described in Cooper et al., Methods Enzymol. (1983), 99, 387–402) revealed the presence of phosphoserine and phosphothreonine. Thus, recombinant Ndr is an active serine/threonine protein kinase and can undergo autophosphorylation on at least two sites. These two sites are likely to be located within Ndr itself, since the fusion protein was not able to phosphorylate free GST.

Example 5
Expression and localisation of human Ndr in COS-1 Cells

For the detection of the overexpressed protein a rabbit antiserum ($Ab^{425-465}$) is raised against a synthetic peptide (TARGAIPSYMKAAK), derived from the predicted carboxy terminus of human Ndr (SEQ ID NO:7), which is conjugated to keyhole limpet haemocyanin as described in Hendrix et al., J. Biol. Chem. (1993), 268, 7330–7337. Antibody titer is tested (Hendrix et al., J. Biol. Chem. (1993), 7330–7337) on western blots containing lysates of E. coli expressing recombinant Ndr (from example 4). Peptide-specific antibodies are purified on columns of protein A-Sepharose® (Pharmacia) followed by Affi-Gel 10® (Bio-Rad) to which the immunogenic peptide had been coupled following the manufacturer's recommendations. Antibodies are eluted with 50 mM Tris-HCl, pH 7.4 containing 6 M urea, and dialysed extensively against PBS.

COS-1 cells (ATCC CRL 1650) are maintained in DMEM supplemented with 10% FCS at 37° C. For transfection, cells are incubated in DMEM containing 0.7 µg/ml plasmid DNA from pECE-punk (see example 2) and 7 µl/ml Lipofectin® (Gibco BRL). After 5 h, an equal volume of DMEM/20% FCS was added. The transfection is terminated 12 h later by replacing the medium with fresh DMEM/10% FCS, or by passaging the cells onto glass coverslips (for immunolocalisation). Protein expression is analysed 24 h later via immunoblotting.

Immunoblotting is carried out as described in Hendrix et al., J. Biol. Chem. (1993), 268, 7330–7337, using $Ab^{452-4656}$ at a dilution of 1:20. The primary antibody is detected using an ECL kit® (Amersham).

The transfection of the human cDNA into COS-1 cells leads to the appearance of a ~55 kDa immunoreactive polypeptide on western blots of whole-cell lysates. This species is normally not observed in lysates from cells transfected with the pECE vector alone.

Example 6
Analysis of the subcellular localisation of Ndr

Using the same antibody, cells are analysed by indirect immunofluorescence to assess the subcellular localisation of Ndr.

Immunocytochemical analysis is performed on COS-1 cells which are seeded onto acid-washed, poly-lysine coated glass coverslips 12 h after transfection. Cells are fixed in 3.7% paraformaldehyde/PBS for 20 minutes then permeabilised with acetone (−20° C. for 30 seconds). Non-specific binding is blocked with PBS/3% BSA for 30 minutes at 37° C. Coverslips are incubated sequentially with affinity-purified $Ab^{452-465}$ (1:6 in PBS/0.2% BSA), biotin/goat anti-rabbit IgG (1:100, Amersham) and streptavidin/Texas Red (1:200, Amersham), all at 37° C. Washes are for 3×5 min in PBS/0.2% BSA. Stained cells are viewed with a Leica TCS confocal microscope (40× magnification) equipped with an argon/krypton laser, and projections are assembled from ten scanned sections of ~1 μm.

Cells transfected with the human cDNA show an intense nuclear staining and a weaker cytoplasmic signal.

Example 7
Identification of the nuclear localisation signal

To identify the nuclear localisation signal mutants missing amino acids 1–84, 65–81 and 265–276 respectively are constructed as described in example 4 and analysed as described in example 6.

The following primers are used:

```
SEQ ID NO:8   5'- AAGGATCCATGGCAATGACAGGCTC      -3'
SEQ ID NO:9   5'- TTTCTGCTTTCCTTTTG              -3'
SEQ ID NO:13  5'- GAGTCGTTTCTCCTCATC             -3'
SEQ ID NO:14  5'- ACAAGACTTGGATTGGAAG            -3'
SEQ ID NO:15  5'- TCTAGCTAGCTGGGAATTCATGTTCTG    -3'
SEQ ID NO:16  5'- CATGCCATGGGATTGGAAGATTTTGAG    -3'
```

To generate pECE-punkΔ1–84, nts. 848–1403 of pBLM-punk are amplified by PCR with Pfu polymerase (Stratagene) using primers SEQ ID NO:16 and SEQ ID NO:9. The amplified product is digested with NcoI and EcoRI and cloned between the corresponding sites in pECE-punk.

pECE-punkΔ65–81 is obtained from two PCR products generated from pBLM-punk (example 4) using the primer pairs SEQ ID NO:8/SEQ ID NO:13 and SEQ ID NO:9/SEQ ID NO:14. The amplified products are cut with BamHI and EcoRI respectively and blunt-end ligated to each other between the BamHI and EcoRI sites of pBluescript®. The ligated products are isolated therefrom as a NcoI/EcoRI fragment and used to replace the corresponding wild-type sequence in pECE-punk pECE-punkΔ285–276 is constructed by amplifying a region of plasmid pBLM-punk using primers SEQ ID NO:8 and SEQ ID NO:15. The resulting product is cut with NcoI and NheI and ligated between the same sites in pBLM-punk Following this, a HindIII-NheI fragment is obtained and cloned into HindIII/NheI-cut pECE-punk.

Deletion of amino acids 65–81 has no effect on the nuclear accumulation of Ndr; similarly, deletion of the entire amino terminal domain does not reduce nuclear uptake. Therefore, these sequences do not appear to play a role in the nuclear localisation of Ndr. However, deletion of amino acids 265–276 in the catalytic domain insert leads to a significant redistribution of the expressed protein. Instead of an intense nuclear signal, cells show a more diffuse pattern of staining. In many cells, the nuclei are visible as darker regions against the cytoplasm. The expressed protein is not completely excluded from the nuclei (exclusion from the nucleoli is still visible), but this may be explained by an ability to diffuse slowly into the nucleus, as the size of the deletion mutant is near the cut-off size (40–60 kDa) for passive nuclear entry. Thus, the nuclear localisation signal of Ndr appears to be contained within the peptide KRKA-ETWKRNRR (amino acids 265–276).

DEPOSITS

The following microorganism strains were deposited at the Deutsche Sammiung von Mikroorganismen (DSM), Mascheroder Weg 1b, D-38124 Braunschweig (accession numbers and deposition dates given):

| Name | Deposition Date | Deposition Number |
| --- | --- | --- |
| SDEpunk-12 | 19.12.1994 | DSM 9622 |
| BBZpunk-3a | 19.12.1994 | DSM 9623 |
| BBZpunk-16b | 19.12.1994 | DSM 9624 |

---

What is claimed is:

1. An isolated nucleic acid encoding an Ndr protein kinase, wherein the Ndr protein kinase has at least 50% identity to the human Ndr protein having the same amino acid sequence depicted in SEQ ID NO. 2 or SEQ ID NO. 7, said Ndr protein kinase having serine/threonine kinase activity, calcium-dependent calmodulin minding activity, and nuclear localization activity.

2. Nucleic acid according to claim 1 which possesses all or part of the sequence represented in SEQ ID No. 1 or SEQ ID No. 6 and is 20 nucleotides or more in length.

3. Expression vector comprising a nucleic acid according to claim 1, and, operably linked thereto, a promoter.

4. Expression vector according to claim 3 wherein the polypeptide encoded by the nucleic acid is expressed in the form of a fusion protein.

5. A host cell transformed with a nucleic acid according to claim 1.

* * * * *

UNITED STATES PATENT AND TRADEMARK OFFICE
CERTIFICATE OF CORRECTION

PATENT NO. : 6,040,164
DATED : March 21, 2000
INVENTOR(S) : Hemmings, et. al.

It is certified that error appears in the above-identified patent and that said Letters Patent is hereby corrected as shown below:

Title page, item [30], should read:

Foreign Application Priority Data

Dec. 22, 1994      [EPO] Europe..........................94810746.

Signed and Sealed this

Sixth Day of February, 2001

*Attest:*

Q. TODD DICKINSON

*Attesting Officer*      *Director of Patents and Trademarks*